(12) United States Patent
Whyte et al.

(10) Patent No.: US 9,128,038 B2
(45) Date of Patent: Sep. 8, 2015

(54) ANALYTICAL TEST STRIP WITH CAPILLARY SAMPLE-RECEIVING CHAMBERS SEPARATED BY A PHYSICAL BARRIER ISLAND

(75) Inventors: Lynsey Whyte, Inverness (GB); Scott Sloss, Inverness (GB); David Mccoll, Inverness (GB); Neil Whitehead, Inverness (GB); Antony Smith, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 513 days.

(21) Appl. No.: 13/529,901

(22) Filed: Jun. 21, 2012

(65) Prior Publication Data

US 2013/0341209 A1     Dec. 26, 2013

(51) Int. Cl.
    *G01N 27/327*      (2006.01)
    *G01N 33/49*      (2006.01)
    *B01L 3/00*      (2006.01)

(52) U.S. Cl.
    CPC ........ *G01N 27/3272* (2013.01); *G01N 27/3274* (2013.01); *G01N 33/492* (2013.01); *B01L 3/502* (2013.01); *B01L 2300/0825* (2013.01)

(58) Field of Classification Search
    CPC ................................................. G01N 27/3272
    USPC ........ 204/403.01–403.15; 422/400–402, 412, 422/413, 417, 419
    See application file for complete search history.

(56) References Cited

U.S. PATENT DOCUMENTS

| | | |
|---|---|---|
| 4,945,313 A | 7/1990 | Brilka et al. |
| 5,637,469 A | 6/1997 | Wilding et al. |
| 5,708,247 A | 1/1998 | McAleer et al. |
| 5,951,836 A | 9/1999 | McAleer et al. |
| 6,241,862 B1 | 6/2001 | McAleer et al. |
| 6,284,125 B1 | 9/2001 | Hodges et al. |
| 6,377,894 B1 | 4/2002 | Deweese et al. |
| 6,488,827 B1 | 12/2002 | Shartle |
| 6,521,182 B1 | 2/2003 | Shartle |
| 6,676,815 B1 | 1/2004 | Bhullar et al. |
| 6,733,655 B1 | 5/2004 | Davies et al. |
| 6,855,243 B2 * | 2/2005 | Khan .......................... 205/777.5 |
| 7,022,286 B2 | 4/2006 | Lemke et al. |

(Continued)

FOREIGN PATENT DOCUMENTS

| | | |
|---|---|---|
| WO | 2008030757 A1 | 3/2008 |
| WO | WO 2010/049669 A1 | 5/2010 |

OTHER PUBLICATIONS

L. Shrimanth Sudheer, et al. "Microcontroller based phase meter," Journal of Instrument Soc. Of India, KA, India, Mar. 2009, vol. 39 No. 1, pp. 62-64.

(Continued)

*Primary Examiner* — Alex Noguerola

(57) ABSTRACT

An analytical test strip for the determination of an analyte (such as glucose and/or hematocrit) in a bodily fluid sample (such as a whole blood sample) includes a first capillary sample-receiving chamber, a second capillary sample-receiving chamber, and a physical barrier island disposed between the first and second capillary sample-receiving chambers. Moreover, the physical island barrier is disposed such that bodily fluid sample flow between the first capillary sample-receiving chamber and the second capillary sample-receiving chamber is prevented during use of the analytical test strip.

10 Claims, 6 Drawing Sheets

(56) References Cited

U.S. PATENT DOCUMENTS

| | | |
|---|---|---|
| 7,199,594 B2 | 4/2007 | Kermani |
| 7,316,766 B2 * | 1/2008 | Chen et al. ............... 204/403.01 |
| 7,323,098 B2 | 1/2008 | Miyashita et al. |
| 7,338,639 B2 | 3/2008 | Burke et al. |
| 7,718,439 B2 | 5/2010 | Groll |
| 7,955,484 B2 | 6/2011 | Cai et al. |
| 2005/0023137 A1 | 2/2005 | Bhullar et al. |
| 2005/0023152 A1 | 2/2005 | Surridge et al. |
| 2007/0084734 A1 | 4/2007 | Roberts et al. |
| 2007/0087397 A1 | 4/2007 | Kraft et al. |
| 2007/0123801 A1 | 5/2007 | Goldberger et al. |
| 2008/0083618 A1 | 4/2008 | Neel et al. |
| 2009/0095623 A1 | 4/2009 | Boiteau et al. |
| 2010/0041571 A1 | 2/2010 | Cohen et al. |
| 2010/0075340 A1 | 3/2010 | Javanmard et al. |
| 2010/0170791 A1 | 7/2010 | Lee |
| 2010/0270174 A1 | 10/2010 | Chen et al. |
| 2010/0326846 A1 | 12/2010 | Leong |
| 2011/0094896 A1 | 4/2011 | Macfie et al. |

OTHER PUBLICATIONS

International Search Report issued in related International Patent Application No. PCT/GB2013/051552, dated Aug. 16, 2013, 3 pages.

International Preliminary Report on Patentability with Written Opinion issued in related International Patent Application No. PCT/GB2013/051552, dated Dec. 23, 2014, 8 pages.

* cited by examiner

ANALYTICAL TEST STRIP WITH CAPILLARY SAMPLE-RECEIVING CHAMBERS SEPARATED BY A PHYSICAL BARRIER ISLAND

BACKGROUND OF THE INVENTION

1. Field of the Invention

The present invention relates, in general, to medical devices and, in particular, to analytical test strips and related methods.

2. Description of Related Art

The determination (e.g., detection and/or concentration measurement) of an analyte in a fluid sample and/or the determination of a characteristic of a fluid sample (such as haematocrit) are of particular interest in the medical field. For example, it can be desirable to determine glucose, ketone bodies, cholesterol, lipoproteins, triglycerides, acetaminophen and/or HbA1c concentrations in a sample of a bodily fluid such as urine, blood, plasma or interstitial fluid. Such determinations can be achieved using analytical test strips, based on, for example, visual, photometric or electrochemical techniques. Conventional electrochemical-based analytical test strips are described in, for example, U.S. Pat. Nos. 5,708, 247, and 6,284,125, each of which is hereby incorporated in full by reference.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, analytical test strips (e.g., electrochemical-based analytical test strips) for the determination of an analyte (such as glucose and/or hematocrit) in a bodily fluid sample (for example, whole blood) according to embodiments of the present invention include a first capillary sample-receiving chamber, a second capillary sample-receiving chamber, and a physical barrier island disposed between the first and second capillary sample-receiving chambers. Moreover, the physical island barrier is disposed such that bodily fluid sample flow between the first capillary sample-receiving chamber and the second capillary sample-receiving chamber is prevented during use of the analytical test strip.

Analytical test strips according to embodiments of the present invention are beneficial in that, for example, the physical barrier island serves to maintain the fluidic integrity of the first and second capillary sample-receiving chambers while also being easily manufactured. Such fluidic integrity beneficially prevents mixing of reagents and reaction byproducts between the first and second capillary sample-receiving chambers that can lead to inaccuracies in analyte or bodily fluid sample characteristic determination. Moreover, since the physical barrier island can be relatively small, sample application openings for the first and second capillary sample application chambers can be juxtaposed close to one another (for example, separated by a distance of approximately 250 microns that can be operatively bridged by a whole blood sample of approximately 1 micro-liter) such that the single application of a bodily fluid sample bridges both sample application openings and fills both the first and the second capillary sample-receiving chambers. Furthermore, the physical barrier island can be manufactured in a relatively simple and inexpensive manner using manufacturing conventional techniques.

Figure 1:
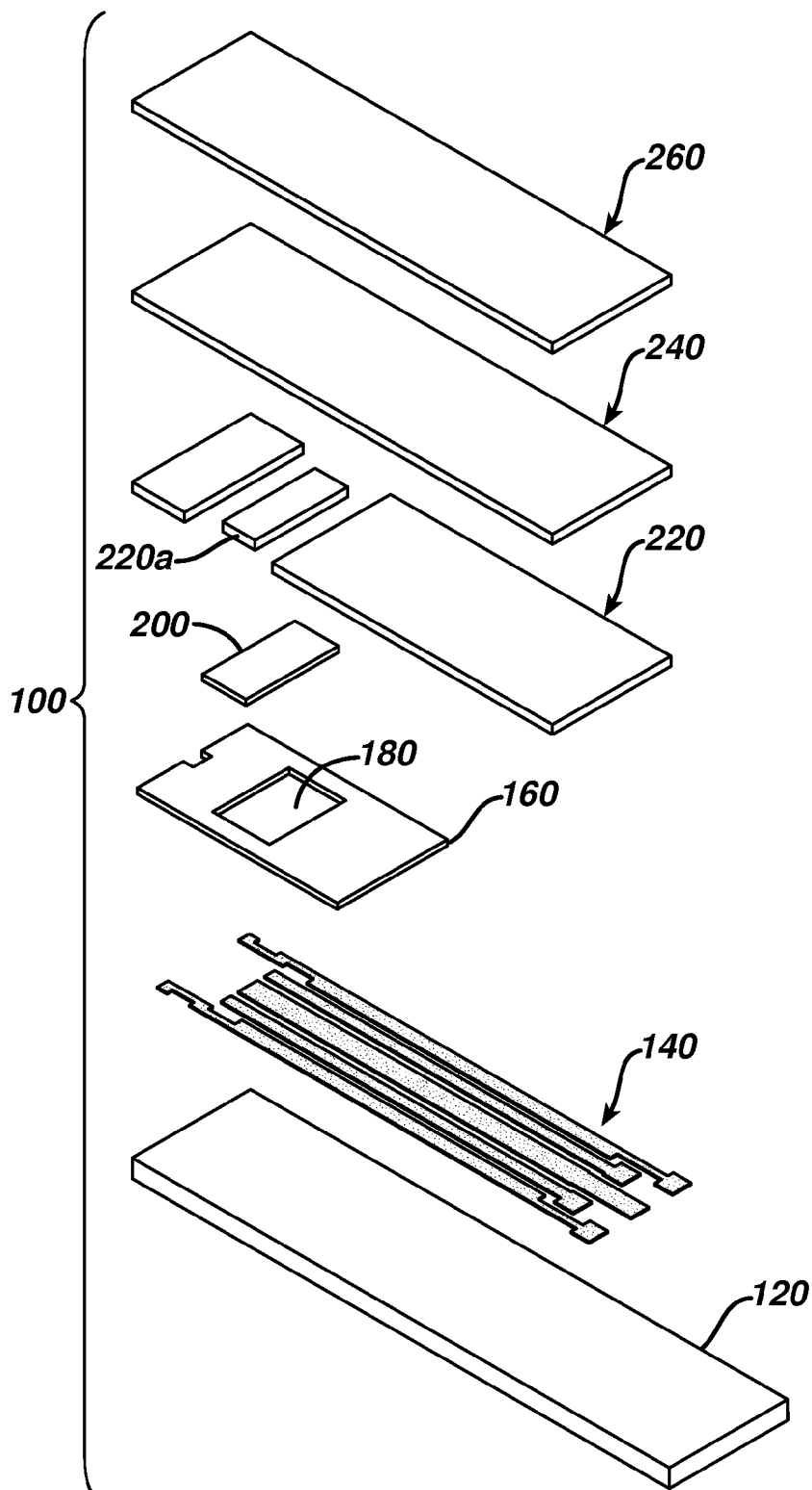
FIG. 1 is a simplified exploded view of an electrochemical-based analytical test strip according to an embodiment of the present invention.
Figure 2:
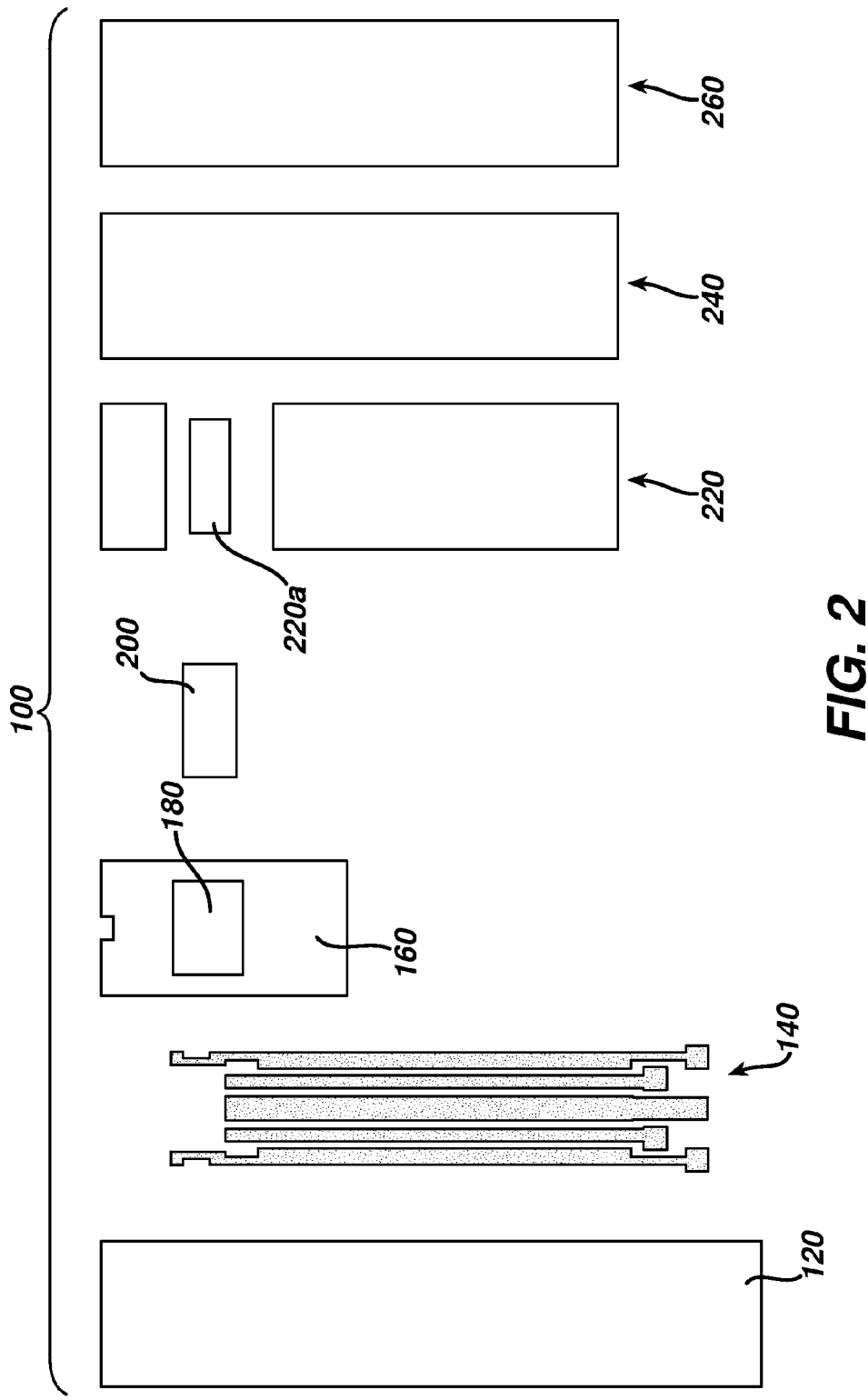
FIG. 2 is a sequence of simplified top views of the various layers of the electrochemical-based analytical test strip of FIG. 1.
Figure 3:
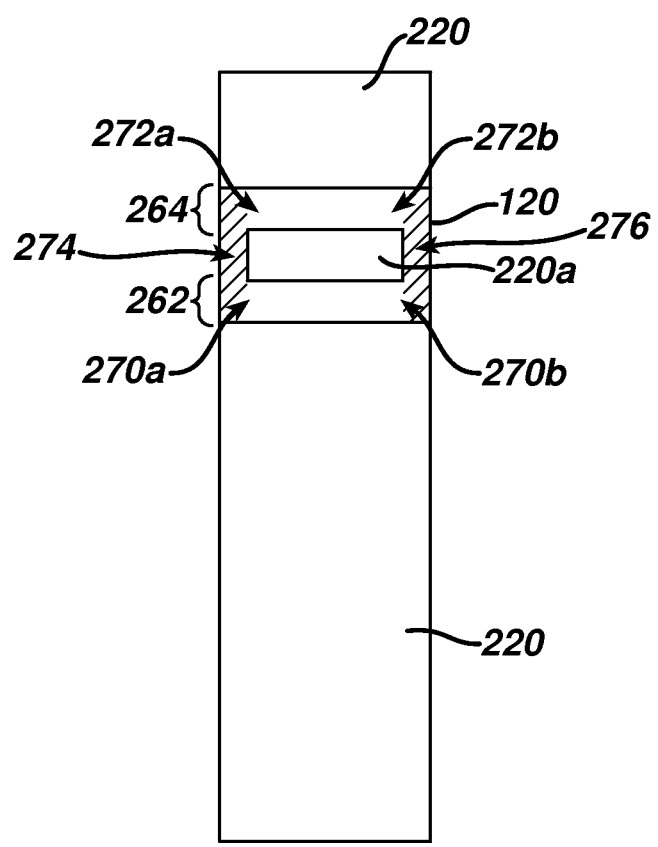
FIG. 3 is a simplified top view representation of the substrate layer and spacer layer of the electrochemical-based analytical test strip of FIG. 1.
Figure 4:
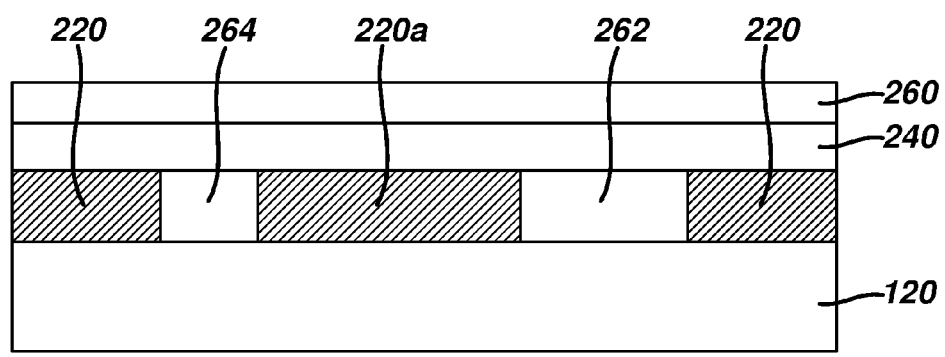
FIG. 4 is a simplified side view of a portion of the electrochemical-based analytical test strip of FIG. 1 that, for clarity, omits the reagent layer, patterned insulation layer and patterned conductor layer thereof.
Figure 5:
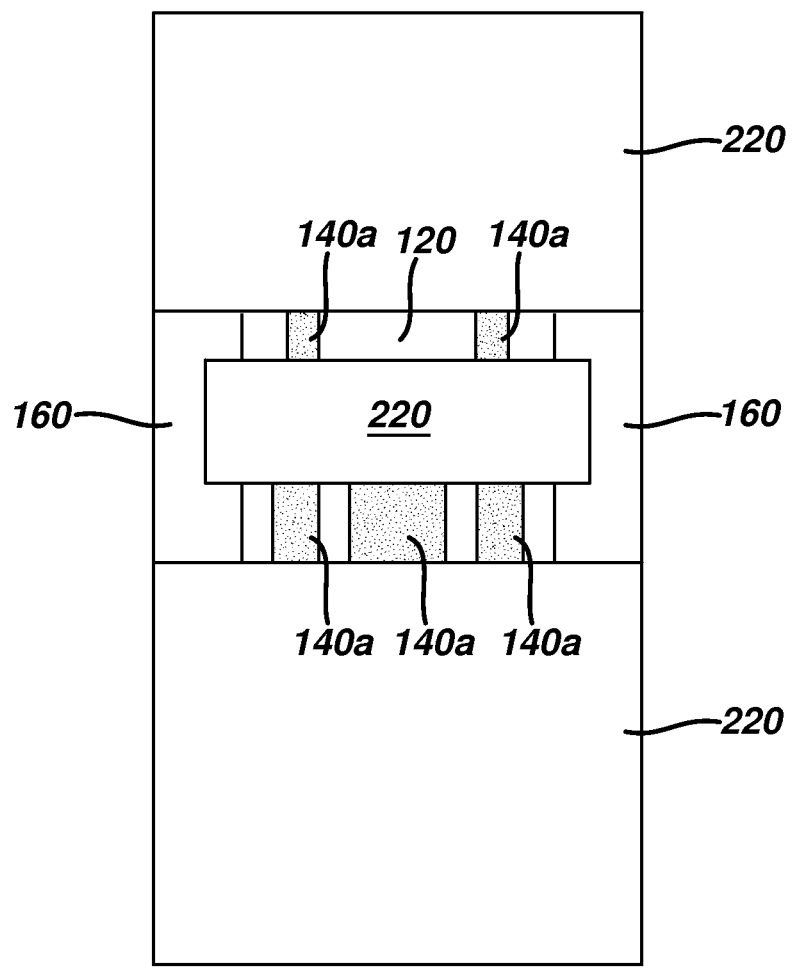
FIG. 5 is a simplified top view of the electrochemical-based analytical test strip of FIG. 1 depicting various components thereof.

FIG. 1 is a simplified exploded view of an electrochemical-based analytical test strip 100 according to an embodiment of the present invention. FIG. 2 is a sequence of simplified top views of the various layers of electrochemical-based analytical test strip 100. FIG. 3 is a simplified top view representation of the substrate layer and spacer layer (a portion of which is configured as a physical barrier island) of electrochemical-based analytical test strip 100. FIG. 4 is a simplified side view of a portion of electrochemical-based analytical test strip 100 that, for clarity, omits the reagent layer, patterned insulation layer and patterned conductor layer thereof. FIG. 5 is a simplified top view of electrochemical-based analytical test strip 100 depicting various components, including the electrodes, thereof.

Referring to FIGS. 1-5, electrochemical-based analytical test strip 100 for the determination of an analyte (such as glucose) in a bodily fluid sample (for example, a whole blood sample) includes an electrically-insulating substrate layer 120, a patterned conductor layer 140, a patterned insulation layer 160 with electrode exposure window 180 therein, an enzymatic reagent layer 200, a patterned spacer layer 220 that includes a physical barrier island 220a, a hydrophilic layer 240, and a top layer 260.

The disposition and alignment of electrically-insulating substrate layer 120, patterned conductor layer 140 (which a variety of electrodes 140a, see FIG. 5 in particular), patterned insulation layer 160, enzymatic reagent layer 200, patterned spacer layer 220 (and physical barrier island 220*a* thereof), hydrophilic layer 240 and top layer 260 of electrochemical-based analytical test strip 100 are such that a first capillary sample-receiving chamber 262 and a second capillary sample-receiving chamber 264 of electrochemical-based analytical test strip 100 are defined.

Physical barrier island 220*a* is disposed between first capillary sample-receiving chamber 262 and second capillary sample-receiving chamber 264 such that fluid flow therebetween during use of electrochemical-based analytical test strip 100 is prevented.

It should be noted that in the embodiments depicted in FIGS. 1-5 the physical barrier island is disposed essentially parallel to the primary flow direction of a bodily fluid that is filling the first and second capillary sample-receiving chambers. The physical barrier island, therefore, does not prevent bodily fluid from filling the first and second capillary sample-receiving chambers but rather prevents bodily fluid that has entered either of the capillary sample-receiving chambers from entering the other capillary sample-receiving chamber.

In the perspective of FIG. 4, first and second capillary sample-receiving chambers 262 and 264 have a height of approximately 100 μm, a width in the range of approximately 1.45 mm to 1.65 mm, and a pitch of approximately 2.55 mm. The abrupt change in vertical dimension that creates the stop junctions is an additional height of approximately 100 μm.

Patterned conductor layer 140, including electrodes 140*a*, of electrochemical-based analytical test strip 100 can be formed of any suitable conductive material including, for example, gold, palladium, platinum, indium, titanium-palladium alloys and electrically conducting carbon-based materials including carbon inks. Referring in particular to FIG. 5, electrode exposure window 180 of patterned insulation layer 160 exposes three electrodes 140*a* in the lower portion of the FIG. (for example, a counter/reference electrode and first and second working electrodes) configured for the electrochemical determination of an analyte (glucose) in a bodily fluid sample (whole blood). Electrode exposure window 180 also exposes two electrodes (in the upper portion of the FIG.) configured for the determination of haematocrit in whole blood. The determination of haematocrit using electrodes of an analytical test strip is described in, for example, U.S. Patent Application Nos. 61/581,100; 61/581,097; 61/581,089; 61/530,795 and 61/530,808, each of which is hereby incorporated in full by reference.

During use, a bodily fluid sample is applied to electrochemical-based analytical test strip 100 and fills both the first and second capillary sample-receiving chambers by capillary action and, thereby, operatively contacts the electrodes disposed in the first and second capillary sample-receiving chambers. Referring to FIG. 3 in particular, first capillary sample-receiving chamber 262 has at least one sample application opening (namely two openings 270*a* and 270*b*) and second capillary sample-receiving chamber 264 has at least one sample application opening (namely, two sample application openings 272*a* and 272*b*). Each of the first and second capillary sample-receiving chambers are configured such that a sample can be applied and fill both of the capillary sample-receiving chambers from either the left-hand side (using sample application openings 270*a* and 272*a*) of the analytical test strip or the right-hand-side (using sample application openings 270*b* and 272*b*). In either circumstance, the sample application opening of the first capillary sample-receiving chamber and the sample application opening of the second capillary sample-receiving chamber are juxtaposed such that a single bodily fluid sample can be simultaneously applied thereto.

In the embodiments of FIGS. 1-5, physical barrier island 220*a* has a width that is less than the width of the electrochemical-based analytical test strip (see FIG. 3 in particular, where "width" in this context refers to a horizontal dimension in the perspective of FIG. 3). In other words, although physical barrier island 220*a* is disposed longitudinally along the first and second capillary sample-receiving chambers, the physical barrier island does not extend to the lateral edges of the electrochemical-based analytical test strip.

The aforementioned lesser width and disposition of physical barrier island 220*a* serves define a first shared sample entry chamber 274 at the first sample application opening 270*a* of the first capillary sample-receiving chamber 262 and the first sample application opening 272*a* of the second capillary sample-receiving chamber 264, and a second shared sample entry chamber 276 at the second sample application opening 270*b* of the first capillary sample-receiving chamber 262 and the second sample application opening 272*b* of the second capillary sample-receiving chamber 264. For clarity, the area of first and second shared sample entry chambers 274 and 276 is shown with cross-hatching in FIG. 3.

First shared sample entry chamber 274 and second shared sample entry chamber 276 are beneficial in that, for example, an applied bodily fluid sample can more easily overcome surface tension forces to fill a such a single shared sample entry chamber (and subsequently fill the first and second capillary sample-receiving chambers), as opposed to overcoming the surface tension of two separate sample entry chambers. In addition, the width (in this context the vertical direction of FIG. 3) of either of the first and second shared sample entry chambers is greater than the width of either of the first or second sample application openings and is also greater than the sum of the widths of both of the first sample application openings or the sum of the widths of both of the second sample application openings. Therefore, a user can more easily apply a bodily fluid sample to such relatively large width in comparison to the width of a sample application opening of a capillary sample-receiving chamber.

Electrically-insulating substrate layer 120 can be any suitable electrically-insulating substrate layer known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, or a polyester substrate. The electrically-insulating substrate layer can have any suitable dimensions including, for example, a width dimension of about 5 mm, a length dimension of about 27 mm and a thickness dimension of about 0.35 mm.

Electrically-insulating substrate layer 120 provides structure to the strip for ease of handling and also serves as a base for the application (e.g., printing or deposition) of subsequent layers (e.g., a patterned conductor layer). It should be noted that patterned conductor layers employed in analytical test strips according to embodiments of the present invention can take any suitable shape and be formed of any suitable materials including, for example, metal materials and conductive carbon materials.

Patterned insulation layer 160 can be formed, for example, from a screen printable insulating ink. Such a screen printable insulating ink is commercially available from Ercon of Wareham, Mass. U.S.A. under the name "Insulayer."

Patterned spacer layer 220 can be formed, for example, from a screen-printable pressure sensitive adhesive commercially available from Apollo Adhesives, Tamworth, Staffordshire, or other suitable materials such as, for example, polyester and polypropylene. The thickness of patterned spacer layer 220 can be, for example 75 μm. In the embodiment of FIGS. 1 through 5, patterned spacer layer 220 defines an outer wall of the first and second capillary sample-receiving chamber 280.

Hydrophilic layer 240 can be, for example, a clear film with hydrophilic properties that promote wetting and filling of electrochemical-based analytical test strip 100 by a fluid sample (e.g., a whole blood sample). Such clear films are commercially available from, for example, 3M of Minneapolis, Minn. U.S.A. and Coveme (San Lazzaro di Savena, Italy). Hydrophilic layer 240 can be, for example, a polyester film coated with a surfactant that provides a hydrophilic contact angle of less than 10 degrees. Hydrophilic layer 240 can also be a polypropylene film coated with a surfactant or other surface treatment, e.g., a MESA coating. Hydrophilic layer 240 can have a thickness, for example, of approximately 100 µm.

Enzymatic reagent layer 200 can include any suitable enzymatic reagents, with the selection of enzymatic reagents being dependent on the analyte to be determined. For example, if glucose is to be determined in a blood sample, enzymatic reagent layer 200 can include a glucose oxidase or glucose dehydrogenase along with other components necessary for functional operation. Enzymatic reagent layer 200 can include, for example, glucose oxidase, tri-sodium citrate, citric acid, polyvinyl alcohol, hydroxyl ethyl cellulose, potassium ferrocyanide, antifoam, cabosil, PVPVA, and water. Further details regarding enzymatic reagent layers, and electrochemical-based analytical test strips in general, are in U.S. Pat. Nos. 6,241,862 and 6,733,655, the contents of which are hereby fully incorporated by reference.

Top layer 260 can be formed of any suitable mater including, for example, polyester materials, polypropylene materials, and other plastic materials. Top layer 260 can have a thickness, for example of approximately 50 µm.

Electrochemical-based analytical test strip 100 can be manufactured, for example, by the sequential aligned formation of patterned conductor layer 140, patterned insulation layer 160, enzymatic reagent layer 200, patterned spacer layer 220, hydrophilic layer 240 and top layer 260 onto electrically-insulating substrate layer 120. Any suitable techniques known to one skilled in the art can be used to accomplish such sequential aligned formation, including, for example, screen printing, photolithography, photogravure, chemical vapour deposition and tape lamination techniques.

Figure 6:
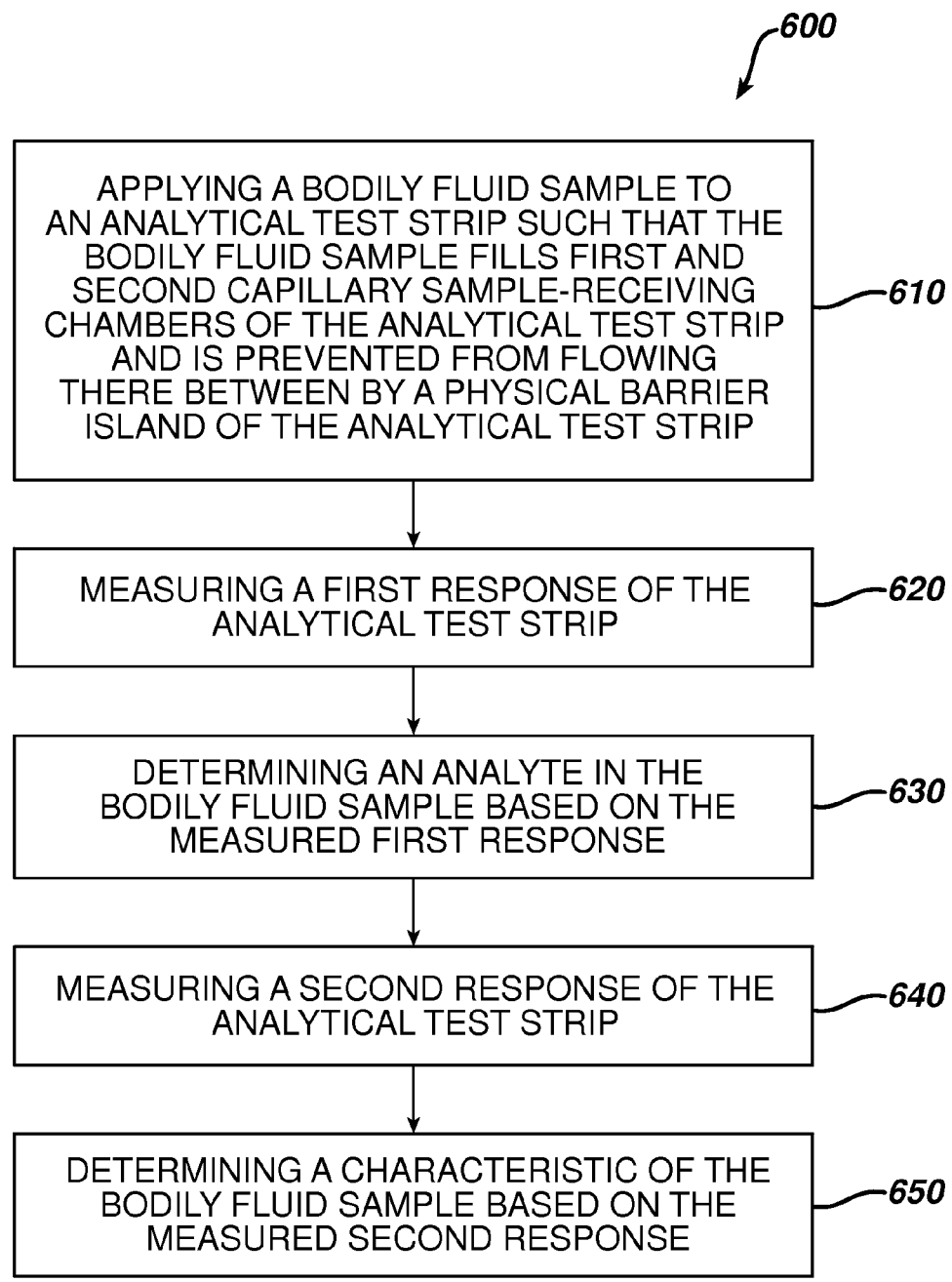
FIG. 6 is a flow diagram depicting stages in a method for determining an analyte in a bodily fluid sample according to an embodiment of the present invention.

FIG. 6 is a flow diagram depicting stages in a method 600 for determining an analyte (such as glucose) in a bodily fluid sample (for example, a whole blood sample) and/or a characteristics of the bodily fluid sample (e.g., hematocrit) according to an embodiment of the present invention. Method 600 includes (see step 610 of FIG. 6) applying a bodily fluid sample to an analytical test strip such that the applied bodily fluid sample fills a first capillary sample-receiving chamber and a second capillary sample-receiving chamber of the analytical test strip and is prevented from flowing between the first capillary sample-receiving chamber and the second capillary sample-receiving chamber by a physical barrier island of the analytical test strip.

Method 600 also includes measuring a first response of the analytical test strip (for example an electrochemical response from electrodes in the first capillary sample-receiving chamber) and determining an analyte in the bodily fluid sample is determined based on the first measured electrochemical response (see steps 620 and 630 of FIG. 6).

In steps 640 and 650 of method 600 also includes, measuring a second response of the analytical test strip (for example, an electrical response from electrodes in the second capillary sample-receiving chamber) and determining a characteristic of the bodily fluid sample based on the second measured response. The measuring and determination steps described above can, if desired, by performed using a suitable associated meter and measurement steps 620 and 630 can be performed in any suitable sequence or in an overlapping manner.

Once apprised of the present disclosure, one skilled in the art will recognize that method 600 can be readily modified to incorporate any of the techniques, benefits and characteristics of analytical test strips according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. An analytical test strip for the determination of an analyte in a bodily fluid sample, the analytical test strip comprising:
    an electrically insulating substrate layer;
    at least one reference electrode and a plurality of working electrodes, all of which are disposed on the electrically insulating substrate layer;
    an enzymatic reagent layer disposed over at least one of, but not all of the working electrodes;
    a first capillary sample-receiving chamber;
    a second capillary sample-receiving chamber;
    a physical barrier island disposed between the first capillary sample-receiving chamber and the second capillary receiving chamber, and
    wherein the physical island barrier is disposed such that bodily fluid sample flow between the first capillary sample-receiving chamber and the second capillary sample-receiving chamber during use of the analytical test strip is prevented.

2. The analytical test strip of claim 1 wherein the first capillary sample receiving chamber has at least one sample application opening and the second sample receiving chamber has at least one sample application opening, and
    wherein the sample application opening of the first capillary sample-receiving chamber and the sample application opening of the second sample-receiving chamber are juxtaposed such that a single bodily fluid sample can be simultaneously applied thereto.

3. The analytical test strip of claim 1 wherein the first capillary sample-receiving chamber has a first sample application opening and a second sample application opening and wherein the second sample-receiving chamber has a first sample application opening and a second sample application opening.

4. The analytical test strip of claim 3 wherein the physical barrier island extends longitudinally along the first capillary sample-receiving chamber and the second capillary sample-receiving chamber.

5. The analytical test strip of claim 4 wherein the physical barrier island is disposed such that:
    a first shared sample entry chamber is defined at the first sample application opening of the first capillary sample-receiving chamber and the first sample application opening of the second capillary-sample receiving chamber, and a second shared sample entry chamber is defined at the second sample application opening of the first capillary sample-receiving chamber and the second sample application opening of the second capillary sample-receiving chamber.

6. The analytical test strip of claim 5 wherein a width of the first shared sample entry chamber is greater than the sum of widths of the first sample application opening of the first capillary sample-receiving chamber and the first sample application opening of the second capillary-sample receiving chamber, and wherein a width of the second shared sample entry chamber is greater than the sum of widths of the second sample application opening of the first capillary sample-receiving chamber and the second sample application opening of the second capillary-sample receiving chamber.

7. The analytical test strip of claim 1 wherein the analytical test strip is configured as an electrochemical-based analytical test strip.

8. The analytical test strip of claim 1 wherein the bodily fluid sample is a whole blood sample.

9. The analytical test strip of claim 1 wherein the analyte is glucose.

10. The analytical test strip of claim 1 wherein the analyte is glucose and the analytical test strip is configured to determine the analyte in a bodily fluid sample introduced to the first capillary sample-receiving chamber and hematocrit of a bodily fluid sample introduced into the second capillary sample-receiving chamber.

* * * * *